US011357930B2

(12) United States Patent
Sonoyama et al.

(10) Patent No.: US 11,357,930 B2
(45) Date of Patent: Jun. 14, 2022

(54) SYRINGE OPENING CONFIRMATION STRUCTURE

(71) Applicant: Taisei Kako Co., Ltd., Osaka (JP)

(72) Inventors: Tomoyuki Sonoyama, Osaka (JP); Shota Masuda, Osaka (JP)

(73) Assignee: Taisei Kako Co., Ltd., Osaka (JP)

( * ) Notice: Subject to any disclaimer, the term of this patent is extended or adjusted under 35 U.S.C. 154(b) by 189 days.

(21) Appl. No.: 16/626,174

(22) PCT Filed: Jun. 26, 2018

(86) PCT No.: PCT/JP2018/024092
§ 371 (c)(1),
(2) Date: Dec. 23, 2019

(87) PCT Pub. No.: WO2019/004158
PCT Pub. Date: Jan. 3, 2019

(65) Prior Publication Data
US 2020/0179619 A1    Jun. 11, 2020

(30) Foreign Application Priority Data
Jun. 26, 2017   (JP) .............................. JP2017-124076

(51) Int. Cl.
*A61M 5/50*     (2006.01)
*A61M 5/31*     (2006.01)
(52) U.S. Cl.
CPC ................ *A61M 5/50* (2013.01); *A61M 5/31* (2013.01)

(58) Field of Classification Search
CPC ........ A61M 5/50; A61M 5/31; A61M 5/5086; A61M 2005/3104; A61M 5/3202; A61M 2205/273
See application file for complete search history.

(56) References Cited

U.S. PATENT DOCUMENTS 6,196,998 B1 * 3/2001 Jansen ................ A61M 5/3134
604/111
6,821,268 B2   11/2004 Balestracci
(Continued)

FOREIGN PATENT DOCUMENTS

DE    102008013198 A1    9/2009
JP    2002-177395 A      6/2002
(Continued)

OTHER PUBLICATIONS

International Preliminary Report on Patentability dated Jan. 9, 2020 in connection with PCT/JP2018/024092.
(Continued)

*Primary Examiner* — Bhisma Mehta
*Assistant Examiner* — Rachel T. Smith
(74) *Attorney, Agent, or Firm* — Brooks Kushman P.C.

(57) ABSTRACT

An object of the present invention is to provide a tamper-evident structure of syringe that enables a user to recognize at a glance the fact that the syringe is already unsealed. A cap 4 of the syringe 2 includes a cover 5 that covers a distal end of a nozzle 21, a sealing plug 7 that is elastic and seals the distal end of the nozzle 21 in a state of being attached to the inside of the cover 5, and a tamper ring 6 that includes a restraining part that is separably connected to the syringe 2 and the cover 5 that presses the sealing plug 7 against the distal end of the nozzle 2.

7 Claims, 11 Drawing Sheets

(56) References Cited

U.S. PATENT DOCUMENTS

| | | |
|---|---|---|
| 7,806,861 B2 | 10/2010 | Witowski |
| 9,861,767 B2 | 1/2018 | Okihara et al. |
| 10,272,212 B2 | 4/2019 | Okihara et al. |
| 2002/0177395 A1 | 11/2002 | Ham et al. |
| 2004/0225258 A1 | 11/2004 | Balestracci |
| 2011/0015578 A1 | 1/2011 | Lowke |
| 2015/0011936 A1* | 1/2015 | Okihara ................ A61M 5/344 604/111 |

FOREIGN PATENT DOCUMENTS

| | | |
|---|---|---|
| JP | 2008-502422 A | 1/2008 |
| JP | 5009924 B | 6/2012 |
| WO | WO2013/146296 A1 | 10/2013 |
| WO | WO2016/026780 A1 | 2/2016 |

OTHER PUBLICATIONS

European Search Report dated Oct. 7, 2020 in connection with related European Patent Appl. No. 18825125.0.

* cited by examiner

SYRINGE OPENING CONFIRMATION STRUCTURE

CROSS REFERENCE TO RELATED APPLICATION

This application claims priority to Japanese Patent Application No. 2017-124076, the disclosure of which is incorporated herein by reference in its entirety.

FIELD

The present invention relates to a tamper-evident structure of a syringe for enabling checking whether the syringe is in an unsealed state.

BACKGROUND

Conventionally, a cap is attached to a nozzle of a syringe for safety and hygiene reasons. Some of such capped syringes have a tamper-evident structure for checking that the seal has once been unsealed.

For example, the tamper-evident structure disclosed in Patent Literature 1 includes a cylindrical adapter that is fixed around a nozzle of a syringe, a closure piece that is fitted onto the adapter while covering the nozzle, and an annular twist-off ring that surrounds the adapter and is detachably connected to the closure piece.

Of the adapter, one opening end in the axial direction (hereinafter, referred to as a first opening end) is arranged on a distal end side of the nozzle, and the other opening end in the axial direction (hereinafter, referred to as a second opening end) is arranged on a shoulder portion side of the syringe.

A helical screw thread is formed on the outer peripheral surface of the adapter on the first opening end side, and a flange protruding radially outward from the outer peripheral surface is formed on the second opening end side of the adapter.

The closure piece is cylindrical and is open only at one end in the axial direction. An internal thread is formed on an inner peripheral surface of one end side of the closure piece.

The twist-off ring is detachably connected to one end of the closure piece.

In the tamper-evident structure of the aforementioned configuration, when the closure piece to which the twist-off ring is connected is tightened to the adapter, the screw thread of the adapter engages with the internal thread of the closure piece to thereby fix the closure piece to the adapter.

Also, when the twist-off ring gets over the flange as the closure piece is tightened to the adapter, the twist-off ring is prevented from falling off from the adapter by the flange.

When unsealing the syringe, a rotation of the closure piece (a rotation in the direction in which the closure piece is loosened from the adapter) allows the closure piece to move away from the twist-off ring in the axial direction along with the rotation. Continued rotation of the closure piece causes separation of the closure piece from the twist-off ring to thereby make the closure piece detach from the adapter.

In this way, the thus configured tamper-evident structure is designed to separate the closure piece and the twist-off ring from each other for unsealing the syringe, and thus, the unsealed state of the syringe can be confirmed by checking the state of connection between the closure piece and the twist-off ring.

CITATION LIST

Patent Literature

Patent Literature 1: JP 5009924 B

SUMMARY

Technical Problem

The aforementioned conventional tamper-evident structure necessitates the threaded engagement of the closure piece with the adaptor. Thus, when the closure piece is again brought into threaded engagement with the adapter, the closure piece can be fixed at the position before the syringe is unsealed even after the syringe has been unsealed. Therefore, this poses a risk of causing a user to erroneously recognize the unsealed state of the syringe because the closure piece and the twist-off ring return to the respective positions before the syringe is unsealed.

In view of the aforementioned circumstances, it is an object of the present invention to provide a tamper-evident structure of syringe that enables instant recognition of the unsealed state of the syringe.

Solution to Problem

The tamper-evident structure of syringe of the present invention includes a cap that is attached to a syringe, the cap comprising: a cover that covers a distal end portion of a nozzle; a sealing plug that is elastic and seals the distal end portion of the nozzle in a state of being attached to the inside of the cover; and a tamper ring that is cylindrical and is fixed to the syringe with the nozzle inserted into the tamper ring, the cover configured to press the sealing plug against the distal end portion of the nozzle in an axial direction of the tamper ring and thereby elastically compress the sealing plug, and the tamper ring comprising a restraining portion that is separably connected to the cover.

The tamper-evident structure of syringe of the present invention may include a locking member that is cylindrical and is fixed to the syringe with the nozzle inserted therethrough, wherein the locking member is insertable into the tamper ring in the axial direction, and wherein the tamper ring has an inner peripheral surface and the locking member has an outer peripheral surface, on which anti-drop engaging portions are respectively formed to engage with each other.

The tamper-evident structure of syringe of the present invention may include an anti-rotation structure for preventing the tamper ring from rotating in a circumferential direction centered on the axial direction, wherein the anti-rotation structure comprises a first anti-rotation engaging portion formed on the syringe and a second anti-rotation engaging portion formed on the tamper ring, and the first anti-rotation engaging portion and the second anti-rotation engaging portion are configured to be engageable with each other in the circumferential direction.

In the tamper-evident structure of syringe of the present invention, the locking member may include an anti-rotation abutting portion that is configured to abut against the anti-drop engaging portion of the tamper ring in the circumferential direction centered on the axial direction.

Further, in the tamper-evident structure of syringe of the present invention, the locking member may include a fixed part that is threaded into the inside of a peripheral wall formed around the nozzle in a state where the locking member is inserted through the nozzle, and the rocking member comprises an anti-rotation portion that prevents rotation with respect to the peripheral wall.

DESCRIPTION OF EMBODIMENTS

Hereinafter, a tamper-evident structure of a syringe according to one embodiment of the present invention will be described with reference to the accompanying drawings. In this embodiment, the tamper-evident structure will be described by taking, for example, a capped syringe.

Figure 1:
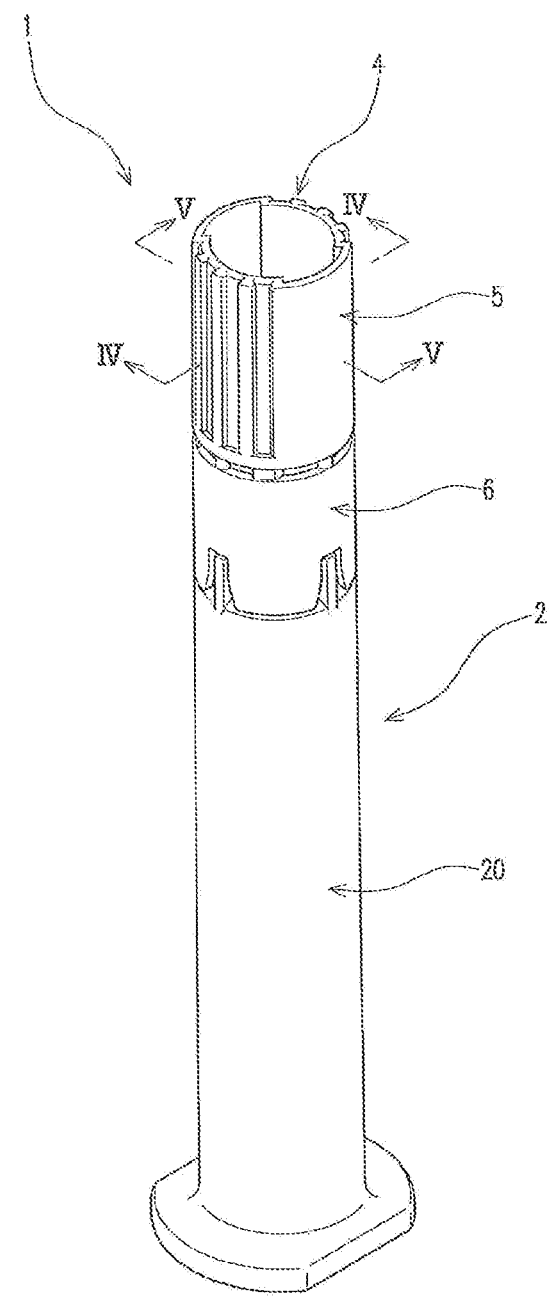
FIG. 1 is a perspective view of a capped syringe according to one embodiment of the present invention.
Figure 2:
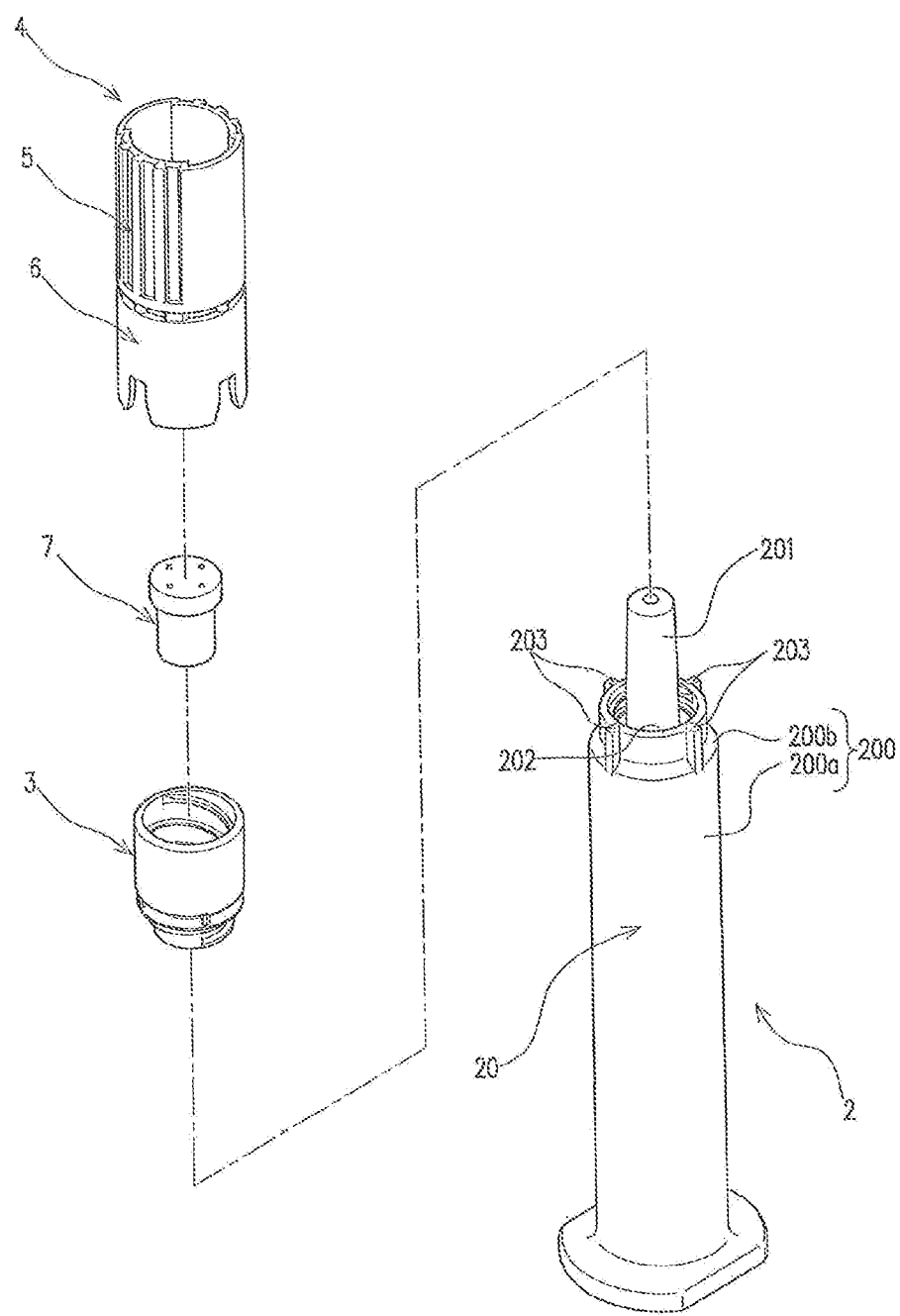
FIG. 2 is an exploded view of the capped syringe according to the embodiment.

As shown in FIG. 1 and FIG. 2, a syringe 2 includes an outer cylinder 20 configured to be filled with a liquid such as a medicine. The outer cylinder 20 may be provided with a plunger although not shown in FIG. 1 and FIG. 2.

As shown in FIG. 2, the outer cylinder 20 has a barrel 200 that has a cylindrical shape, a nozzle 201 that is provided at one end in the axial direction of the barrel 200, a peripheral wall 202 that is provided on the barrel 200 so as to surround the nozzle 201, and an anti-rotation rib 203 formed on the outside of the peripheral wall 202.

The barrel 200 has a cylindrical portion 200a that has a cylindrical shape and has the same or substantially the same outer diameter and inner diameter over the entire length in the axial direction, and a shoulder portion 200b that has an outer diameter gradually decreasing as it extends from one end of the cylindrical portion 200a in the axial direction. In this embodiment, the following description will be made by referring to the axial direction of the barrel 200 (cylindrical portion 200a) simply as the axial direction, referring to the direction orthogonal to the axial direction as the radial direction, and referring to the circumferential direction centered on the axial direction simply as the circumferential direction.

Figure 3:
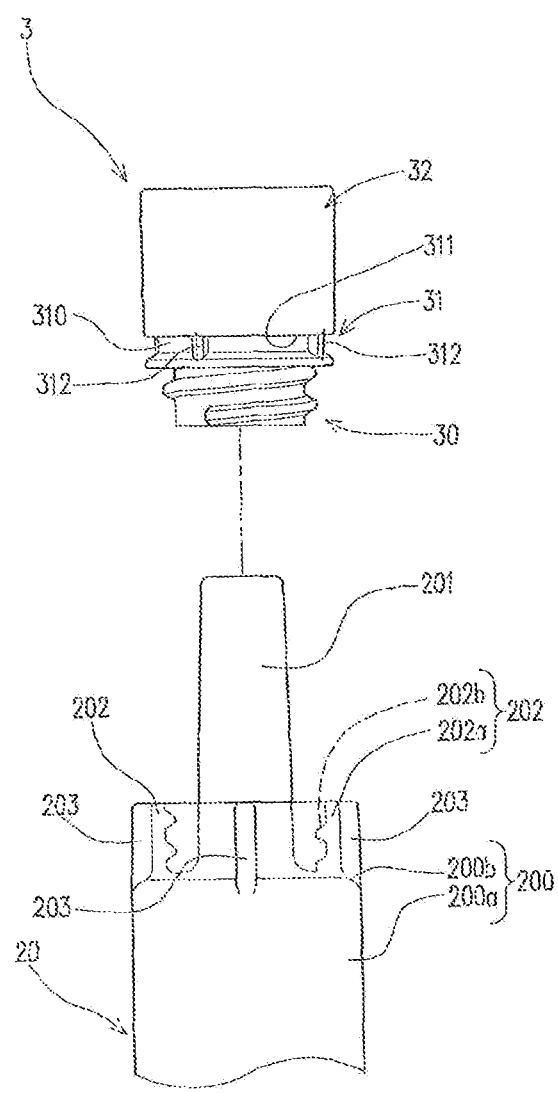
FIG. 3 is an enlarged view of a locking member and a syringe of the capped syringe according to the embodiment.

As shown in FIG. 3, the nozzle 201 extends from the distal end of the shoulder portion 200b, and is formed to have an outer diameter smaller than the outer diameters of the cylindrical portion 200a and the shoulder portion 200b. The nozzle 201 is formed in a hollow cylindrical shape, and the opening on the proximal end side in the direction in which the nozzle 201 extends from the shoulder portion 200b is in communication with the inside of the barrel 200, and the opening on the distal end side in the extending direction is opened toward the outside.

The peripheral wall 202 has a peripheral wall main body 202a that is annular (annular ring shape in this embodiment) and extends from the shoulder portion 200b in the axial direction, and a fixing portion 202b for fixing a locking member 3 to be described later to the peripheral wall main body 202a.

The outer diameter of the peripheral wall 202 is smaller than the outer diameter of the cylindrical portion 200a. Therefore, the outer peripheral surface of the peripheral wall 202 is located on the inner side of the outer peripheral surface of the cylindrical portion 200a in the radial direction, and therefore a step is formed between the cylindrical portion 200a and the peripheral wall 202.

The inner diameter of the peripheral wall 202 is larger than the outer diameter of the nozzle 201. Therefore, a space is formed between the inner peripheral surface of the peripheral wall 202 and the outer peripheral surface of the nozzle 201.

The fixing portion 202b is formed by an internal thread formed on the inner peripheral surface of the peripheral wall main body 202a, and can restrict the motion of the locking member 3 in the axial direction.

The anti-rotation rib 203 extends linearly along the axial direction, and in this embodiment, extends from the distal end of the peripheral wall main body 202a to the shoulder portion 200b along the axial direction. In this embodiment, a plurality of (four) anti-rotation ribs 203 are arranged at intervals in the circumferential direction.

The locking member 3 will now be described. The locking member 3 is a member formed in a cylindrical shape, and is configured to be attachable to the syringe 2 (peripheral wall 202) with the nozzle 201 inserted through one opening (see FIG. 5).

The locking member 3 according to this embodiment has a fixed portion 30 that is fixed to the peripheral wall 202, an anchoring portion 31 that is provided to be continuous with the fixed portion 30, and a connecting portion 32 that is connected integrally with the fixed portion 30 via the anchoring portion 31.

The fixed portion 30 is cylindrical, and a thread is formed on an outer peripheral surface thereof. Therefore, the locking member 3 is attached to the peripheral wall 202 by bringing the fixed portion 30 into threaded engagement with the fixing portion 202b.

The anchoring portion 31 is cylindrical, and the inner space thereof communicates with the inner space of the fixed portion 30. A recessed engagement groove 310 is formed on the outer peripheral surface of the anchoring portion 31.

In this embodiment, the engagement groove 310 is formed so as to be continuous over the entire circumference of the outer peripheral surface of the anchoring portion 31, and an inner surface 311 on one side in the axial direction (in the groove width direction of the engagement groove 310) extends outward in the radial direction from the bottom surface of the anchoring portion 31.

In the engagement groove 310 according to this embodiment, a plurality of anti-rotation abutting portions 312 are formed so as to be arranged at intervals in the circumferential direction. Each of the anti-rotation abutting portions 312 is formed so as to provide blocks in the engagement groove 310 in the circumferential direction.

The connecting portion 32 is also cylindrical, and the internal space thereof communicates with the internal space of the fixed portion 30 and the internal space of the anchoring portion 31.

The locking member 3 according to this embodiment is configured such that, while being mounted on the syringe 2 (a state in which the fixed portion 30 is attached to the fixing portion 202b), the distal end of the connecting portion 32 (an opposite end to one end connected to the anchoring portion 31) is arranged at a position away from the distal end of the nozzle 201 toward the proximal end side of the nozzle 201 in the axial direction.

Further, the connecting portion 32 has an internal thread formed on the inner peripheral surface to enable an external device (e.g., an injection needle, a three-way stopcock, or the like) for connection to the nozzle 201 to be attached to the nozzle 201 using the internal thread. As seen from the above, the locking member 3 according to this embodiment also serves as an adaptor for securing the connected state of the external device to the nozzle 201.

As shown in FIG. 2, the cap 4 includes a cover 5 for protecting the distal end portion of the nozzle 201, a tamper ring 6 that is detachably connected to the cover 5, and a sealing plug 7 (see FIG. 5) for closing (sealing) the opening of the distal end of the nozzle 201 in the cover 5.

Figure 4:
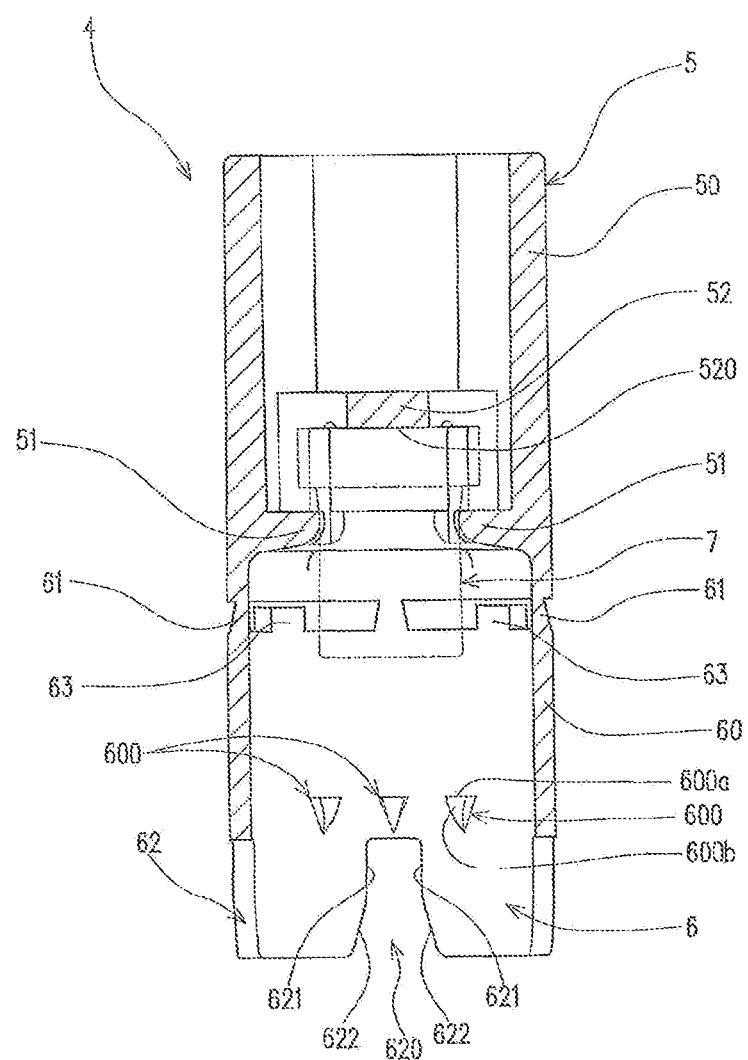
FIG. 4 is a cross-sectional view of a cap taken along the line IV-IV in FIG. 1.

As shown in FIG. 4, the cover 5 has an exterior portion 50 that is cylindrical, a holding portion 51 for holding the sealing plug 7 in the exterior portion 50, and a pressing portion 52 for pressing (compressing) the sealing plug 7 held by the holding portion 51 toward the distal end of the nozzle 201 in the axial direction.

The distal end portion of the nozzle 201 is inserted into the exterior portion 50 from one opening. In this embodiment, one end on one opening side of the exterior portion 50 is referred to as a proximal end, and one end on the other opening side is referred to as a distal end.

The outer diameter of the exterior portion 50 is the same as or substantially the same as the outer diameter of the cylindrical portion 200a. In the state where the cap 4 is attached to the syringe 2, the axial direction of the exterior portion 50 coincides with the axial direction of the barrel 200.

A plurality of holding portions 51 are provided on the inner peripheral surface on the proximal end side of the exterior portion 50. The plurality of holding portions 51 are arranged at intervals in the circumferential direction. The holding portions 51 protrude from the inner peripheral surface of the exterior portion 50 toward the inner side in the radial direction. In this embodiment, the following description will be made by referring to an area further inside the distal ends of the holding portions 51 as an insertion area.

The pressing portion 52 is located closer to the distal end side of the cover 5 than the holding portion 51 in the axial direction. The pressing portion 52 has a pressing surface 520 formed to face the holding portion 51 side in the axial direction (the proximal end side of the cover 5) and extends in the radial direction.

At least a part of the pressing surface 520 is located further inward of the distal end of the holding portion 51 in the radial direction (on the inner side in the radial direction).

The tamper ring 6 has a retaining ring 60 that is to be mounted on the syringe 2, a restraining portion 61 that protrudes from one opening end of the retaining ring 60 and is detachably connected at its distal end to the cover 5, a rotation stopper 62 that is provided at the other opening end of the retaining ring 60, and a receiving portion 63 that protrudes from one opening end of the retaining ring 60 and is aligned with the restraining portion 61 in the circumferential direction.

The retaining ring 60 has a plurality of engaging protrusions 600 that protrude from the inner peripheral surface. Each of the engaging protrusions 600 includes an engagement surface 600a that is formed on the distal end side of the cap 4 and is composed of a plane extending in the radial direction, and an inclined surface 600b formed so as to be gradually directed in the radially outward direction from the engagement surface 600a as it advances toward the proximal end of the cap 4.

The restraining portion 61 has a tapered shape. Further, in this embodiment, a plurality of restraining portions 61 are formed so as to be aligned at certain intervals relative to one opening end of the retaining ring 60.

One end (distal end) of the rotation stopper 62 in the axial direction is provided at the other opening end of the retaining ring 60. An insertion groove 620 that opens at the other end (proximal end) in the axial direction is formed in the rotation stopper 62.

The insertion groove 620 extends along the axial direction. The groove width on the bottom side of the insertion groove 620 is constant, and the groove width on the opening side of the insertion groove 620 gradually increases as the groove advances away from the bottom side increases.

Therefore, a pair of side edges on the bottom side of the insertion groove 620 (hereinafter, referred to as the bottom side edge portions 621) extend parallel to each other along the axial direction, and the pair of side edges on the opening side (hereinafter, referred to as the opening side edge portions 622) are inclined so that the distance from each other gradually increases as they advance away from the bottom side.

A plurality of receiving portions 63 are formed so as to be aligned at certain intervals relative to one opening end of the retaining ring 60. In this embodiment, the receiving portion 63 and the restraining portion 61 are alternately arranged relative to one opening end of the retaining ring 60.

The amount of extension of the receiving portion 63 from the one opening end is smaller than the amount of extension of the restraining portion 61. Therefore, the distal end of the receiving portion 63 is located closer to the tamper ring 6 than the distal end of the restraining portion 61, so that, when the cover 5 is connected to the distal end of the restraining portion 61, a gap is formed between the cover 5 and the receiving portion 63.

Figure 5:
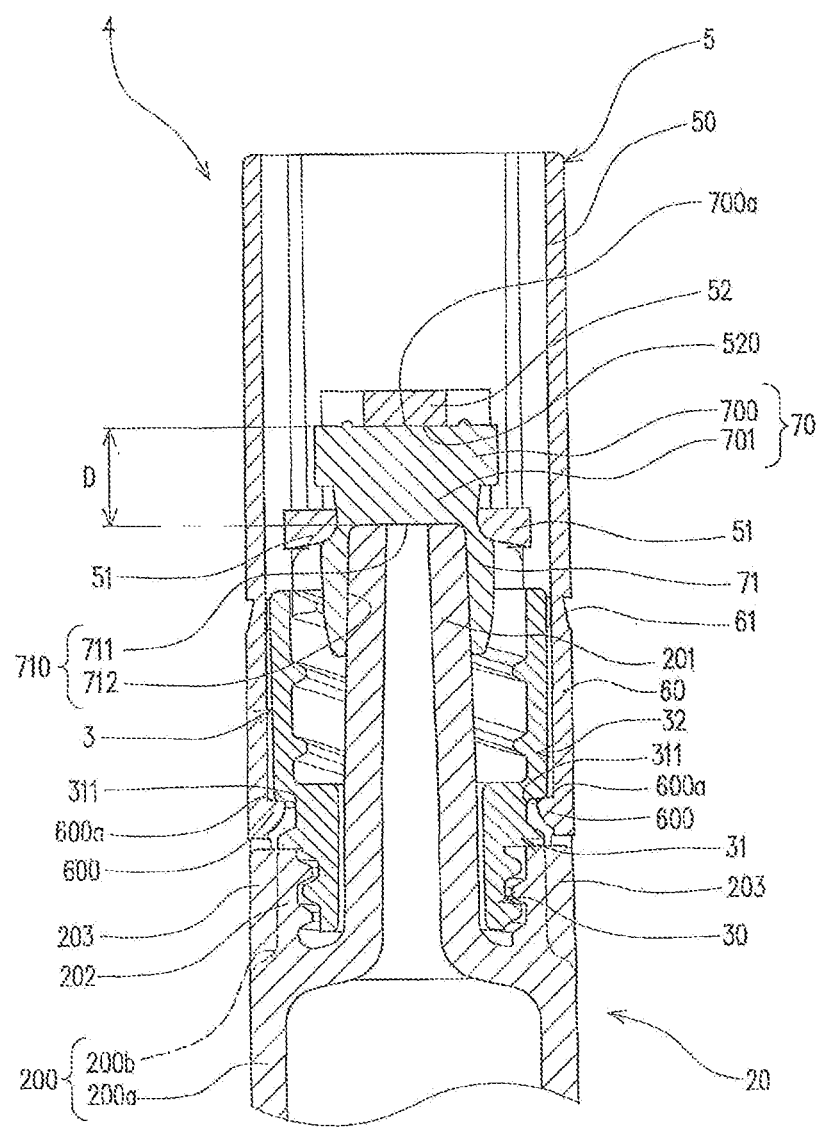
FIG. 5 is an enlarged cross-sectional view of the capped syringe taken along the line V-V in FIG. 1.

The sealing plug 7 has elasticity. Further, as shown in FIG. 5, the sealing plug 7 has a held portion 70 for being held in the cover 5, and a closing portion 71 that is formed integrally with the held portion 70 and provided for closing the opening of the distal end of the nozzle 201.

The held portion 70 has a head portion 700 that is disposed between the holding portion 51 and the pressing portion 52, and an extending portion 701 that extends from the head portion 700 and is held by the plurality of holding portions 51 in a state of being inserted into the insertion area.

One end surface of the head portion 700 in the axial direction is an abutment surface 700a that abuts against the pressing surface 520.

The outer diameter of the extending portion 701 is smaller than the outer diameter of the head portion 700, and the outer peripheral surface of the extending portion 701 is located inside the outer peripheral surface of the head portion 700 over the entire circumference.

The closing portion 71 is provided with a press-fit recess 710 that opens toward the outside, and the distal end of the nozzle 201 is press-fitted into the press-fit recess 710.

A bottom surface 711 of the press-fit recess 710 is configured to be held in close contact with the distal end surface of the nozzle 201, and an inner peripheral surface 712 of the press-fit recess 710 is configured to be held in close contact with the outer peripheral surface of the nozzle 201. The size of the press-fit recess 710 is preferably smaller than the size of the nozzle 201.

The configuration of the capped syringe 1 according to this embodiment is as described above. Next, the description will be made for the manner of assembling the capped syringe 1 and the manner of use.

When the capped syringe 1 according to this embodiment is to be assembled, the nozzle 201 of the syringe 2 in which the locking member 3 is mounted is inserted into the cap 4 in which the cover 5 and the tamper ring 6 are connected by the restraining portion 61 and the sealing plug 7 is mounted in the cover 5.

According to the above manner, the distal end portion of the nozzle 201 is press-fitted into the press-fit recess portion 710 of the sealing plug 7, the bottom surface 711 is held in close contact with the distal end surface of the nozzle 201, and the inner peripheral surface 712 is held in close contact with the outer peripheral surface of the nozzle 201 over the entire circumference.

Further, the bottom surface 711 of the sealing plug 7 is pushed toward the pressing portion 52 (pressing surface 520) side by the distal end portion of the nozzle 201, so that the sealing plug 7 is compressed in the axial direction by the pressing portion 52 and the distal end portion of the nozzle 201. Therefore, the size of the sealing plug 7 in the axial direction (the distance D from the abutment surface 700a to the bottom surface 711) is reduced.

When the locking member 3 is inserted into the inside of the tamper ring 6, and the engagement groove 310 of the locking member 3 reaches a position corresponding in the axial direction to the engaging protrusions 600 of the tamper ring 6, the engaging protrusions 600 fit into the engagement groove 310. This causes the inner surface 311 in the engagement groove 310 and the engagement surfaces 600a of the engaging protrusions 600 to engage with each other in the axial direction and thus prevents the cap 4 as a whole from dropping from the syringe 2.

That is, the inner surface 311 of the engagement groove 310 and the engagement surface 600a of the engaging protrusion 600 respectively serve as anti-drop engagement portions that engage with each other in the axial direction, and the tamper ring 6 is prevented from dropping from the locking member 3 by the anti-drop engaging portions.

Thereby, the cover 5 is connected via the restraining portions 61 to the tamper ring 6 fixed to the syringe 2, while the plug portion 7 covering the distal end portion of the nozzle 201 is compressed in the axial direction.

Further, when the peripheral wall main body 202a is inserted into the inside of the rotation stopper 62 and the anti-rotation rib 203 is inserted into the inside of the insertion groove 620, the anti-rotation rib 203 is disposed at a position adjacent to the bottom side edge portions 621 and the opening side edge portions 622 in the circumferential direction. Therefore, even if a rotational force acts on the cap 4, the rotation of the tamper ring 6 and the rotation stopper 62 with respect to the syringe 2 is restricted due to the mutual interaction between the anti-rotation rib 203 and the bottom side edge portions 621 in the circumferential direction.

Figure 6:
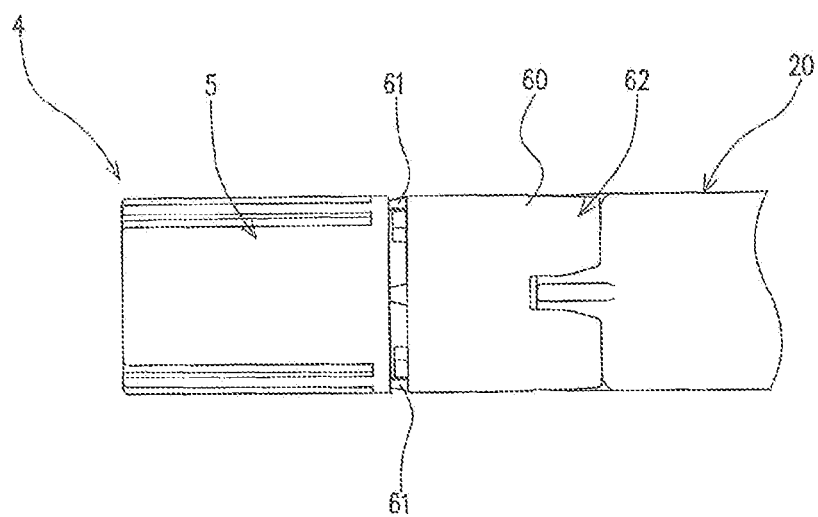
FIG. 6 is an explanatory view of the capped syringe before unsealing.
Figure 7:
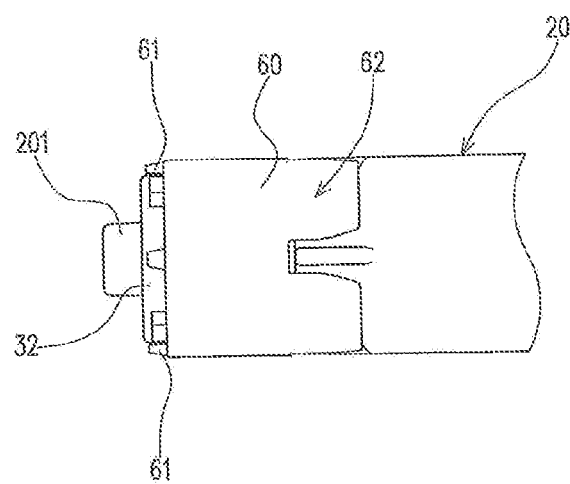
FIG. 7 is an explanatory view of the capped syringe after unsealing.

When the capped syringe 1 assembled as described above is to be unsealed, a user holds the syringe 2 or the tamper ring 6 by one hand, and twists the cover 5 in the circumferential direction by another hand to break the restraining portions 61. Thus, the cover 5 is separated from the tamper ring 6, and thus, when the cover 5 is detached, the distal end portion of the nozzle 201 can be exposed (see FIG. 6 and FIG. 7).

Further, when the cover 5 is separated from the tamper ring 6, the cover 5 is released from the restraint by the restraining portion 61, and thus the sealing plug 7 and the distal end portion of the nozzle 201 are released from the compression state by the pressing portion 52. This causes the sealing plug 7 in the cover 5 to elastically recover, and thus the size of the sealing plug 7 in the axial direction (the distance D from the abutment surface 700a to the bottom surface 711) after unsealing becomes larger than that before unsealing.

Accordingly, after unsealing, even when the distal end portion of the nozzle 201 is held inserted into the press-fit recess portion 710, a gap is formed between the cover 5 and the restraining portions 61 (a cut portion of the restraining portions 61).

Figure 8:
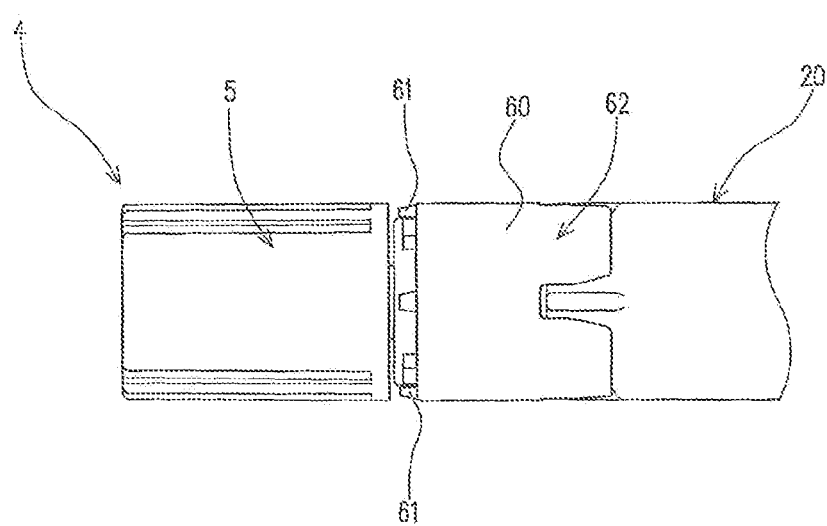
FIG. 8 is an explanatory view of the capped syringe when a nozzle is covered with a sealing plug after unsealing.

Further, after unsealing, even if the distal end portion of the nozzle 201 is inserted into the cover 5 that has been detached once and additionally the distal end portion of the nozzle 201 is pushed into the press-fit recess portion 710 to compress the sealing plug 7, the motion of the cover 5 in the axial direction cannot be restrained, and therefore, the cover 5 is pushed back by the sealing plug 7 that elastically recovers. Therefore, the cover 5 and the restraining portion 61 return to the state in which a gap is formed therebetween (see FIG. 8).

As described above, according to the capped syringe 1 of this embodiment, it is possible to form a gap in the cut portion of the restraining portion 61 due to the elastical recovery of the sealing plug 7 caused by the cutting of the restraining portion 61 (unsealing of the syringe 2), and further possible to enable prevention of the motion of the cover 5 from being restricted (restrained) even if the sealing plug 7 is covered on the distal end portion of the nozzle 201 again after unsealing, that is, to enable prevention of the sealing plug 7 from being held compressed by the cover 5.

Thus, the capped syringe 1 of this embodiment makes it possible to prevent the cover 5 and the restraining portions 61 can be prevented from being seen as if they are connected to each other despite the syringe has been unsealed, since it includes the cover 5 of the cap 4, the sealing plug 7 and the tamper ring 6, and the tampering constitutes a tamper-evident structure having the restraining portions 61 that are separably connected to the cover 5 that is held in a state where the sealing plug 7 is pressed against the distal end portion of the nozzle 201 in the axial direction and thereby held elastically compressed.

Accordingly, the capped syringe 1 can exert an excellent effect of enabling a user to recognize at a glance the fact that the syringe 2 is already unsealed.

Further, according to the capped syringe 1 of this embodiment, the relative rotation of the syringe 2 with respect to the tamper ring 6 is restricted by the engagement of the anti-rotation rib 203 of the syringe 2 with the bottom side edge portion 621 of the tamper ring 6 in the circumferential direction.

Thus, according to this embodiment, since the anti-rotation rib 203 of the syringe 2 and the bottom side edge portion 621 of the tamper ring 6 act as a first anti-rotation engaging portion and a second anti-rotation engaging portion that engage with each other in the circumferential direction, and the anti-rotation structure for restricting the rotation of the tamper ring 6 in the circumferential direction is configured by the first anti-rotation engaging portion and the second anti-rotation engaging portion. Thus, when the first anti-rotation engaging portion and the second anti-rotation engaging portion are engaged with each other in the circumferential direction in order to rotate the cap 4 to cut the restraining portions 61, the relative rotation of the syringe 2 with respect to the tamper ring 6 is restricted. This configuration allows for easy rotation of the cover 5 with respect to the tamper ring 6, and hence easy cutting of the restraining portion 61.

According to the capped syringe 1 of this embodiment, the inner surface 311 of the locking member 3 (the locking member 3, of which the motion in the axial direction is restricted), in which the fixed portion 30 is brought into the treaded engagement with the fixing portion 202b, is engaged with the engagement surface 600a of the tamper ring 6 in the axial direction. This configuration allows for the restriction of the motion of the tamper ring 6 in the axial direction. Further, the bottom side edge portion 621 of the rotation stopper 62 connected to the tamper ring 6 and the anti-rotation rib 203 are configured to interfere with each other in the circumferential direction. This configuration allows for the restriction of the rotation in the circumferential direction of the rotation stopper 62 and the tamper ring 6 covering the outside of the locking member 3. Accordingly, the locking member 3 is prevented from dropping from and loosening from the syringe 2 to thereby prevent the locking member 3 from falling off from the syringe 2.

Further, according to the capped syringe 1 of this embodiment, the locking member 3 has the anti-rotation abutting portion 312 that can abut against the engaging protrusion 600 of the tamper ring 6 in the circumferential direction. This allows for the abutment between the engaging protrusion 600 and the anti-rotation abutting portion 312 in the circumferential direction, and hence the restriction of the rotation of the locking member 3 with respect to the tamper ring 6. Thus, the locking member 3 can be prevented from idling in the tamper ring 6.

Further, according to this embodiment, since the syringe 2 and the locking member 3 are separate members, the syringe 2 and the locking member 3 can be formed of different materials. In this case, for example, a resin having a hardness higher than that of the syringe 2 can be employed as the material of the locking member 3. Thus, the fitting force between the locking member 3 and the external device is increased to be able to enhance the effect of preventing an external device from falling off from the locking member 3.

Further, according to the capped syringe 1 of this embodiment, the anti-drop engaging portions (the inner surface 311, the engagement surface 600a) that engage with each other in the axial direction are formed respectively on the inner peripheral surface of the tamper ring 6 and the outer peripheral surface of the locking member 3. This configuration allows for attachment of the tamper ring 6 to the locking member 3 and prevention of the tamper ring 6 from dropping from the locking member 3 merely by the insertion of the locking member 3 into the tamper ring 6 in the axial direction. Accordingly, the prevention of the cap 4 from dropping from the outer cylinder 20 and prevention of the cap 4 from rotating with respect to the outer cylinder 20 can be made by one operation, and thus the capped syringe 1 can be smoothly assembled.

When the syringe 2 is inserted into the cap 4 from the nozzle 201 side, the engaging protrusion 600 is pushed outward in the radial direction by the outer peripheral surface of the connecting portion 32. However, the engaging protrusion 600 that includes the inclined surface 600b can suppress hooking or catching of the distal end of the locking member 3 with the engaging protrusion 600. Thus, the outer cylinder 20 can be smoothly inserted into the cap 4.

Further, according to the capped syringe 1 of this embodiment, the threaded engagement of the fixed portion 30 of the locking member 3 into the peripheral wall 202, and the formation of the engagement groove 310 on the outer surface of the anchoring portion 31 of the locking member 3 for engagement with the engaging protrusion 600 of the tamper ring 6 can suppress the strength reduction of the peripheral wall 202.

Further, according to this embodiment, the tamper ring 6 is attached to the locking member 3 that is mounted to the nozzle 201. This configuration allows for prevention of the external force applied to the tamper ring 6 from directly acting on the nozzle 201, and hence prevention of damage of the nozzle 201.

According to the capped syringe 1 of this embodiment, a step is formed between the cylindrical portion 200a and the peripheral wall 202 by making the outer diameter of the peripheral wall 202 smaller than the outer diameter of the cylindrical portion 200a. This configuration allows the outer peripheral surface of the rotation stopper 62 to be accommodated in the step (between the outer peripheral surface of the cylindrical portion 200a and the outer peripheral surface of the peripheral wall 202). Further, each of the outer diameter of the rotation stopper 62, the outer diameter of the retaining ring 60, and the outer diameter of the cover 5 is set to be the same as or substantially the same as the outer diameter of the barrel 200. This configuration allows the outer shape of the capped syringe 1 to be a straight shape without a step between the outer cylinder 20 and the cap 4, which enhances easy transportation and storage.

The tamper-evident structure of the present invention and the capped syringe provided with the tamper-evident structure are not limited to the aforementioned embodiment, and it is matter of course that various modifications can be made without departing from the gist of the present invention.

In the aforementioned embodiment, four anti-rotation ribs 203 are formed on the peripheral wall main body 202a, but the number of anti-rotation ribs 203 may be three or less or five or more.

In the aforementioned embodiment, the locking member 3 is configured to have both the function for fixing the cap 4 to the syringe 2 and the function for connecting an external device to the syringe 2, but is not limited to this configuration. For example, the locking member 3 may be configured to have only the function for fixing the cap 4 to the syringe 2. In this case, an internal thread may not be formed on the inner peripheral surface of the connecting portion 32.

Figure 9:
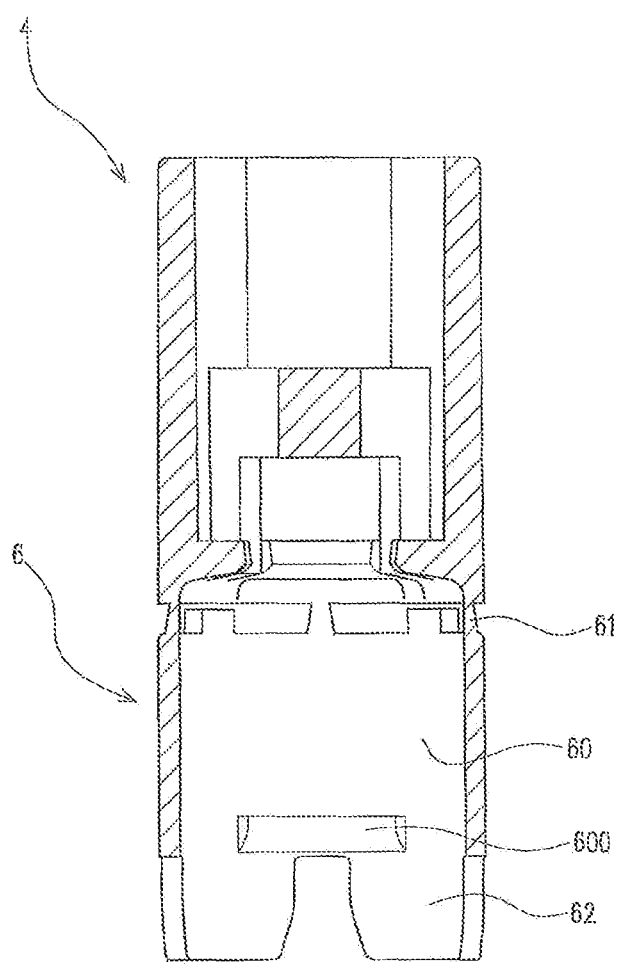
FIG. 9 is a longitudinal cross-sectional view of a cap and a tamper ring of a capped syringe according to another embodiment of the present invention.
Figure 10:
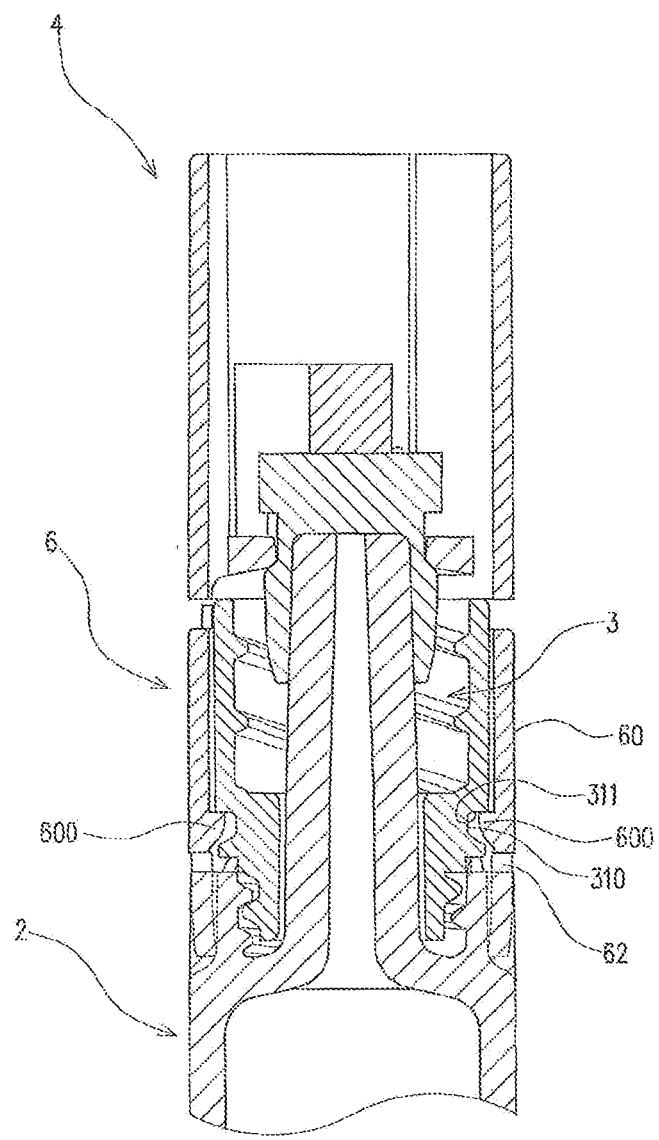
FIG. 10 is an enlarged longitudinal cross-sectional view of the capped syringe according to the other embodiment.

In the aforementioned embodiment, a group of engaging protrusions constituted by a plurality of engaging protrusions 600 that are formed as a group on the inner peripheral surface of the retaining ring 60 is arranged at a position opposite to the retaining ring 60 in the radial direction, but the present invention is not limited to this configuration. For example, as shown in FIG. 9 and FIG. 10, a single engaging protrusion 600 extending along the circumferential direction of the inner peripheral surface may be formed on the inner peripheral surface of the retaining ring 60 at a position opposite to the retaining ring 60 in the radial direction. This configuration increases the rigidity of the engaging protrusion 600, and thereby increases the engagement force between the engaging protrusion 600 and the engagement groove 310 (inner surface 311) of the locking member 3. Thus, the tamper ring 6 is hardly pulled out of the locking member 3 (see FIG. 10).

In the aforementioned embodiment, the tamper ring 6 is prevented from rotating with respect to the syringe 2, and then the locking member 3 is prevented from rotating with respect to the tamper ring 6, to thereby prevent the locking member 3 from rotating with respect to the syringe 2 (peripheral wall 202), but the present invention is not limited to this configuration. For example, it may be configured to prevent the rotation of the locking member 3 with respect to the syringe by direct engagement of the locking member 3 with the syringe 2.

Figure 11:
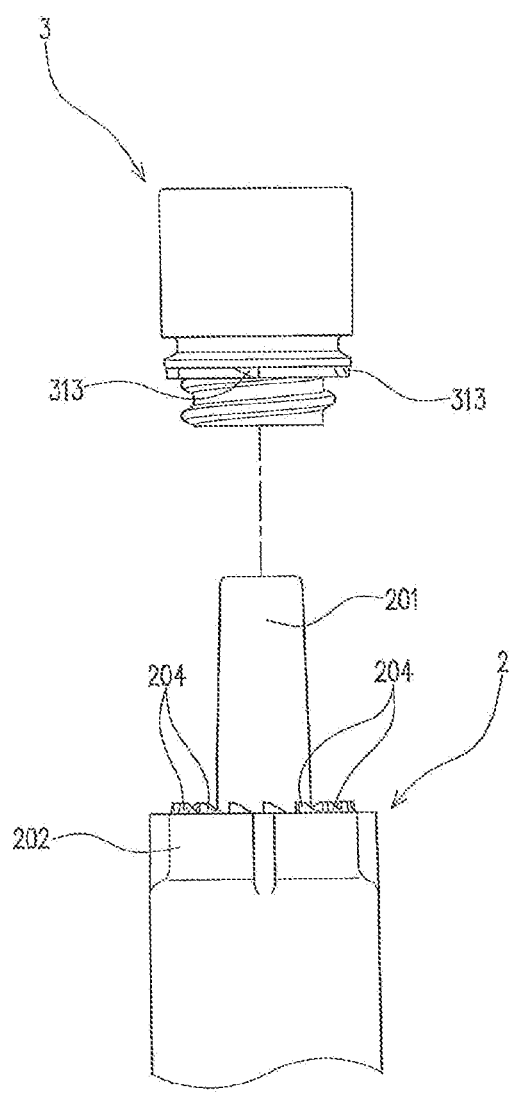
FIG. 11 is an enlarged view of a main part of a capped syringe according to still another embodiment of the present invention.

In this case, for example, as shown in FIG. 11, a syringe side engaging portion 204 protruding from the distal end surface of the peripheral wall 202 and a locking member side engaging portion 313 protruding from the opposite surface of the locking member 3 to the distal end surface of the peripheral wall 202 may be provided to be engaged with each other in the rotational circumferential direction of the locking member 3. This configuration allows for prevention of the rotation of the locking member 3 with respect to the peripheral wall 202 (rotation of the locking member 3 in the direction in which the threaded engagement with the peripheral wall 202 is loosened). Further, it is also possible to prevent the rotation of the locking member 3 with respect to the peripheral wall 202 by increasing the frictional force generated in a sliding portion between the locking member 3 and the peripheral wall 202.

When the locking member 3 is configured to be directly engaged with the syringe 2 to prevent the rotation of the locking member 3 with respect to the syringe 2, the anti-rotation abutting portions 312 of the locking member 3 may not be provided.

The tamper-evident structure of the aforementioned embodiment is configured to engage the engaging protrusions 600 with the inner surface 311 of the engagement groove 310 to prevent the cap 4 from falling off from the syringe 2, but is not limited thereto. For example, the tamper-evident structure may be configured to prevent the cap 4 from falling off from the syringe 2 by welding the tamper ring 6 to the syringe 2 or the locking member 3. Such falling-off prevention measure may be made by the engagement of the engaging protrusions 600 with the inner surface 311 of the engagement groove 310, and further welding of the tamper ring 6 to the syringe 2 or the locking member 3.

Although not specifically mentioned in the aforementioned embodiment, the amount of liquid remaining in the nozzle 201 when the injection is given can be reduced by reducing the volume inside the nozzle 201 of the syringe 2 by reducing the inner diameter of the nozzle 201. In this case, the nozzle 201 preferably has an inner diameter on the distal end side of 2.9 mm or less and an inner diameter on the proximal end side of 3.6 mm or less, and the nozzle 201 more preferably has a height of 7.5 mm to 14.0 mm.

REFERENCE SIGNS LIST

1: Capped syringe
2: Syringe
3: Locking member
4: Cap
5: Cover
6: Ring
7: Sealing plug
20: Outer cylinder
30: Fixed portion
31: Anchoring portion
32: Connecting portion
50: Exterior portion
51: Holding portion
52: Pressing portion
60: Retaining ring
61: Restraining portion
62: Rotation stopper
63: Receiving portion
70: Held portion
71: Closing portion
200: Barrel
200a: Cylindrical portion
200b: Shoulder portion
201: Nozzle
202: Peripheral wall
202a: Peripheral wall main body
202b: Fixing portion
203: Anti-rotation rib
204: Syringe side engaging portion
310: Engagement groove
311: Inner surface
312: Anti-rotation abutting portion
313: Locking member side engaging portion
520: Pressing surface
600: Engaging protrusion
600a: Engagement surface
600b: Inclined surface
620: Insertion groove
621: Bottom side edge portion
622: Opening side edge portion
700: Head portion
700a: Abutment surface
701: Extending portion
10: Press-fit recess
711: Bottom surface
712: Inner peripheral surface
D: Distance

The invention claimed is:

1. A tamper-evident structure of a syringe comprising: a cap that is attached to a syringe;
the cap comprising: a cover that covers a distal end portion of a nozzle; a sealing plug that is elastic and seals the distal end portion of the nozzle in a state of being attached to an inside of the cover; and a tamper ring that is cylindrical and is fixed to the syringe with the nozzle inserted into the tamper ring, and
the tamper ring comprising a restraining portion that is separably connected to the cover in a state where the sealing plug is pressed against the distal end portion of the nozzle in an axial direction of the tamper ring and thereby elastically compressed within the cover,
the cover comprising:
an exterior portion that is cylindrical;
a plurality of holding portions for holding the sealing plug in the exterior portion, the plurality of holding portions aligning at a distance from each other in a circumferential direction around the axial direction, the holding portions protruding from an inner peripheral surface of the exterior portion that is cylindrical toward an inner side in a radial direction; and
a pressing portion for pressing the sealing plug held by the plurality of holding portions toward the distal end of the nozzle in the axial direction, the pressing portion being located closer to a distal end side of the cover than the plurality of holding portions.

2. The tamper-evident structure of the syringe according to claim 1 comprising a locking member that is cylindrical and is fixed to the syringe with the nozzle inserted therethrough,
  wherein the locking member is insertable into the tamper ring in the axial direction, and
    wherein the tamper ring has an inner peripheral surface and the locking member has an outer peripheral surface, on which anti-drop engaging portions are respectively formed to engage with each other.

3. The tamper-evident structure of the syringe according to claim 2,
  wherein the locking member comprises an anti-rotation abutting portion that is configured to abut against the anti-drop engaging portion of the tamper ring in the circumferential direction centered on the axial direction.

4. The tamper-evident structure of the syringe according to claim 2,
  wherein the locking member comprises a fixed part that is threaded into an inside of a peripheral wall formed around the nozzle in a state where the nozzle is inserted through the locking member, and
  the locking member comprises an anti-rotation portion that prevents rotation with respect to the peripheral wall.

5. The tamper-evident structure of the syringe according to claim 1 comprising an anti-rotation structure for preventing the tamper ring from rotating in the circumferential direction centered on the axial direction,
  wherein the anti-rotation structure comprises a first anti-rotation engaging portion formed on the syringe and a second anti-rotation engaging portion formed on the tamper ring, and
  the first anti-rotation engaging portion and the second anti-rotation engaging portion are configured to be engageable with each other in the circumferential direction.

6. The tamper-evident structure of the syringe according to claim 1, wherein the plurality of holding portions contact the sealing plug.

7. The tamper-evident structure of the syringe according to claim 1, wherein the plurality of holding portions are arranged at intervals in the circumferential direction.

\* \* \* \* \*